United States Patent
Du et al.

(10) Patent No.: US 10,679,817 B2
(45) Date of Patent: Jun. 9, 2020

(54) METHOD AND SYSTEM FOR ADJUSTING FOCAL POINT POSITION

(71) Applicant: SHANGHAI UNITED IMAGING HEALTHCARE CO., LTD., Shanghai (CN)

(72) Inventors: Yanfeng Du, Shanghai (CN); Yingbiao Liu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 277 days.

(21) Appl. No.: 15/721,778

(22) Filed: Sep. 30, 2017

(65) Prior Publication Data

US 2018/0358198 A1    Dec. 13, 2018

Related U.S. Application Data

(63) Continuation of application No. PCT/CN2017/087836, filed on Jun. 10, 2017.

(51) Int. Cl.
| | |
|---|---|
| *H01J 35/14* | (2006.01) |
| *H05G 1/30* | (2006.01) |
| *H01J 37/24* | (2006.01) |
| *H05G 1/02* | (2006.01) |

(52) U.S. Cl.
CPC ............ *H01J 35/14* (2013.01); *H01J 35/153* (2019.05); *H01J 37/243* (2013.01); *H05G 1/30* (2013.01); *H05G 1/02* (2013.01)

(58) Field of Classification Search
None
See application file for complete search history.

(56) References Cited

U.S. PATENT DOCUMENTS

| | | | | |
|---|---|---|---|---|
| 4,689,809 A | * | 8/1987 | Sohval | H01J 35/14 378/136 |
| 5,065,420 A | * | 11/1991 | Levene | H01J 35/14 378/121 |
| 6,215,844 B1 | | 4/2001 | Adachi et al. | |
| 6,801,599 B1 | | 10/2004 | Kautz et al. | |

(Continued)

FOREIGN PATENT DOCUMENTS

| | | |
|---|---|---|
| CN | 1552288 A | 12/2004 |
| CN | 103565465 B | 3/2016 |
| JP | 2004095196 A | 3/2004 |

OTHER PUBLICATIONS

Extended European Search Report in European Application No. 17882288.8 dated Jun. 21, 2019, 11 pages.

(Continued)

*Primary Examiner* — Thomas R Artman
(74) *Attorney, Agent, or Firm* — Metis IP LLC

(57) ABSTRACT

The present disclosure relates to a method and system for adjusting a focal point position of an X-ray tube. The method may include: obtaining a first thermal capacity and a first position of a focal point of an X-ray tube; obtaining a second thermal capacity of the X-ray tube; determining a second position of the focal point the X-ray tube based on the second thermal capacity; determining a target grid voltage difference of a focusing cup of the X-ray tube based on the first position and the second position of the focal point; and adjusting the X-ray tube based on the target grid voltage difference.

18 Claims, 12 Drawing Sheets

(56) References Cited

U.S. PATENT DOCUMENTS

| | | | | |
|---|---|---|---|---|
| 7,668,296 B2* | 2/2010 | Schaefer | ................ | H01J 35/06 |
| | | | | 378/136 |
| 8,457,282 B2* | 6/2013 | Baorui | ................ | A61B 6/025 |
| | | | | 378/137 |
| 8,831,178 B2* | 9/2014 | Lemaitre | ................ | H01J 35/06 |
| | | | | 378/136 |
| 8,873,716 B2* | 10/2014 | Ren | ................ | A61B 6/025 |
| | | | | 378/137 |
| 9,484,179 B2* | 11/2016 | Frontera | ................ | H01J 35/14 |
| 2005/0094762 A1 | 5/2005 | Dunham et al. | | |
| 2008/0310593 A1* | 12/2008 | Schaefer | ................ | H01J 35/06 |
| | | | | 378/136 |
| 2010/0119039 A1 | 5/2010 | Miller et al. | | |
| 2010/0303202 A1* | 12/2010 | Ren | ................ | A61B 6/025 |
| | | | | 378/62 |
| 2011/0007866 A1 | 1/2011 | Ishikawa et al. | | |
| 2013/0177130 A1 | 7/2013 | Konno et al. | | |
| 2013/0259192 A1* | 10/2013 | Ren | ................ | A61B 6/025 |
| | | | | 378/21 |
| 2014/0010354 A1* | 1/2014 | Lemaitre | ................ | H01J 35/06 |
| | | | | 378/136 |
| 2014/0056404 A1 | 2/2014 | Poquette et al. | | |
| 2014/0169523 A1* | 6/2014 | Frontera | ................ | H01J 35/14 |
| | | | | 378/62 |
| 2018/0358198 A1* | 12/2018 | Du | ................ | H01J 37/243 |

OTHER PUBLICATIONS

International Search Report in International Application No. PCT/CN2017/087836 dated Jan. 29, 2018, 4 pages.
Writtten opinion in International Application No. PCT/CN2017/087836 dated Jan. 26, 2018, 4 pages.

* cited by examiner

METHOD AND SYSTEM FOR ADJUSTING FOCAL POINT POSITION

CROSS-REFERENCE TO RELATED APPLICATIONS

This application claims priority of International Application No. PCT/CN2017/087836, filed on Jun. 10, 2017, the content of which is expressly incorporated herein by reference to its entirety.

TECHNICAL FIELD

This disclosure generally relates to a method and system for adjusting an X-ray tube, and more particularly, to a method and system for adjusting focal point position of an X-ray tube.

BACKGROUND

A CT image for clinical diagnose is obtained based on data received by a detector. During the imaging process, it is generally assumed that, position of the focal point is fixed. In reality, the focal point position of an X-ray tube may shift due to the change of thermal capacity of the X-ray tube. The shift or offset of the focal point position may bring artifacts on the CT image which may reduce the image quality and influence the results of diagnosis. However, the focal point position is difficult to be measured and the offset of the focal point position is difficult to be corrected.

SUMMARY

In one aspect of the present disclosure, a method is provided. The method may be implemented on at least one device including at least one processor and a storage. The method may include obtaining a first thermal capacity and a first position of a focal point of an X-ray tube; obtaining a second thermal capacity of the X-ray tube; determining a second position of the focal point the X-ray tube based on the second thermal capacity; determining a target grid voltage difference of a focusing cup of the X-ray tube based on the first position and the second position of the focal point; and adjusting the X-ray tube based on the target grid voltage difference.

In some embodiments, the first thermal capacity may be a reference thermal capacity.

In some embodiments, the first thermal capacity may range between 0 and 20% of a maximum thermal capacity.

In some embodiments, the determining the second position of the focal point may include obtaining a first relationship between a position of the focal point and a thermal capacity of the X-ray tube; and determining the second position of the focal point of the X-ray tube based on the second thermal capacity of the X-ray tube and the first relationship.

In some embodiments, the obtaining the first relationship between a position of the focal point and a thermal capacity of the X-ray tube may include obtaining a plurality of training thermal capacities of the X-ray tube; obtaining a plurality of training positions of the focal point of the X-ray tube, wherein each of the plurality of training positions of the focal point of the X-ray tube corresponds to one of the plurality of training thermal capacities of the X-ray tube, respectively; and identifying the first relationship based on the plurality of training thermal capacities of the X-ray tube and the plurality of corresponding training positions of the focal point of the X-ray tube.

In some embodiments, the obtaining a plurality of training positions of the focal point may include measuring a training position of the focal point via a pin hole in a collimator of the X-ray tube.

In some embodiments, the identifying the first relationship may include performing mapping, curve fitting, interpolating, or machine learning based on the plurality of training thermal capacities of the X-ray tube and the plurality of corresponding training positions of the focal point of the X-ray tube.

In some embodiments, the obtaining a first position of the focal point of an X-ray tube may include determining the first position of the focal point based on the first thermal capacity and the first relationship.

In some embodiments, the determining a second position of the focal point may include: obtaining two training thermal capacities of the X-ray tube, wherein the two training thermal capacities are close to the second thermal capacity; obtaining two training positions of the focal point of the X-ray tube corresponding to the two training thermal capacities of the X-ray tube; and determining the second position of the X-ray tube based on the second thermal capacity of the X-ray tube, the two training thermal capacities of the X-ray tube, and the two corresponding training positions of the focal point of the X-ray tube.

In some embodiments, the determining a target grid voltage difference of a focusing cup of the X-ray tube may include: obtaining a second relationship between a grid voltage difference of the focusing cup of the X-ray tube and a position of the focal point of the X-ray tube; and determining the target grid voltage difference of the focusing cup of the X-ray tube based on the first position and the second position of the focal point of the X-ray tube and the second relationship.

In some embodiments, the adjusting the X-ray tube may include adjusting the focal point of the X-ray tube from the second position to the first position.

In another aspect of the present disclosure, a system is provided. The system may include a thermal capacity acquisition unit, a focal point position acquisition unit, a position determination unit, a grid voltage difference determination unit and an adjustment module. The thermal capacity acquisition unit may be configured to obtain a first thermal capacity and a second thermal capacity of an X-ray tube. The focal point position acquisition unit may be configured to obtain a second thermal capacity of the X-ray tube. The position determination unit may be configured to determine a second position of the focal point the X-ray tube based on the second thermal capacity. The grid voltage difference determination unit may be configured to determine a target grid voltage difference of a focusing cup of the X-ray tube based on the first position and the second position of the focal point. The adjustment module may be configured to adjust the X-ray tube based on the target grid voltage difference.

In another aspect of the present disclosure, a non-transitory computer readable medium storing instructions is provided. The instructions, when executed by a computer, causing the computer to implement a method. The method may include: obtaining a first thermal capacity and a first position of a focal point of an X-ray tube; obtaining a second thermal capacity of the X-ray tube; determining a second position of the focal point the X-ray tube based on the second thermal capacity; determining a target grid voltage difference of the focusing cup of the X-ray tube based on the first position and the second position of the focal point; and adjusting the X-ray tube based on the target grid voltage difference.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

Figure 2:
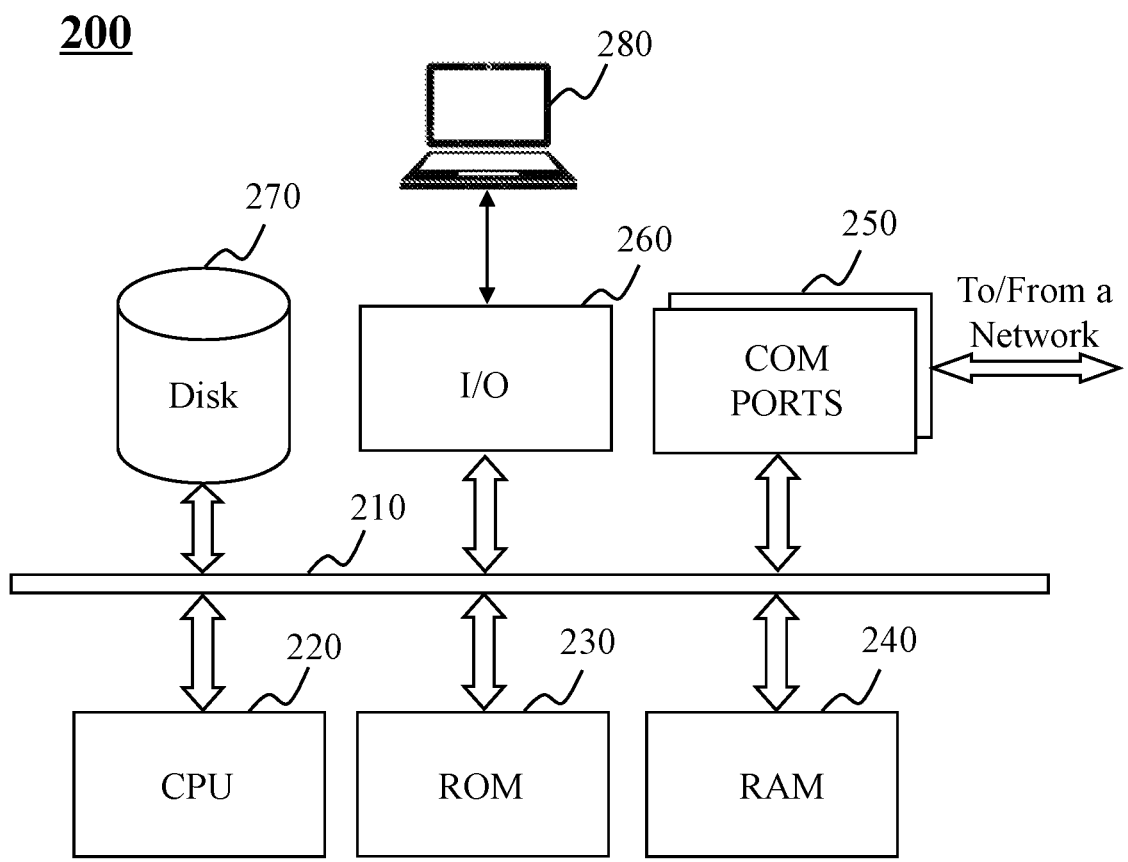
FIG. 2 is a schematic diagram illustrating an exemplary hardware and software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., CPU 220 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

The present disclosure relates to a method and system for adjusting a position of focal point (also referred to as a focal point position) of an X-ray tube of a scanning device, and correcting an offset of the focal point position. The method illustrates a way of estimating the focal point position based on the thermal capacity and a way of adjusting the focal point position or correcting the offset of the focal point position (or abnormal thermal capacity) by adjusting a grid voltage difference of a focusing cup of the X-ray tube. To this end, one or more of the following operations may be performed. A first relationship between a focal point position of the X-ray tube and a thermal capacity of the X-ray tube may be obtained. A second relationship between a focal point position and a grid voltage difference may also be obtained. Furthermore, a working thermal capacity of the X-ray tube may be obtained and compared with a reference thermal capacity of the X-ray tube to assess a difference between the two. Based on the difference in the thermal capacity and the first relationship, an offset of the focal point position may be obtained. A grid voltage difference or a change of grid voltage difference that is needed to correct the offset may be determined based on the offset of the focal point position and the second relationship.

Figure 1:
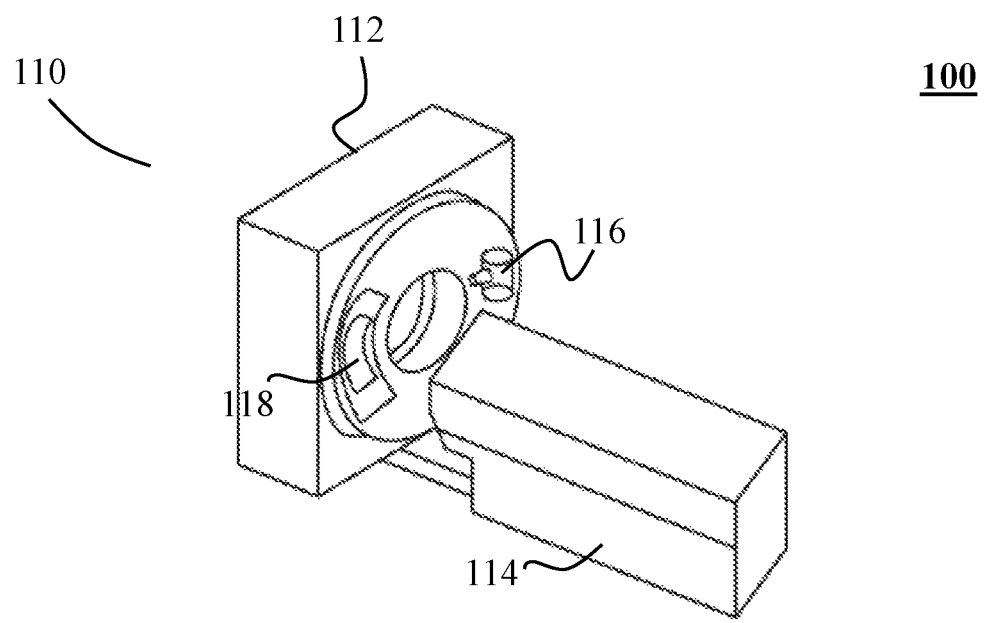
FIG. 1 is a schematic diagram illustrating an exemplary imaging system according to some embodiments of the present disclosure.
Figure 1:
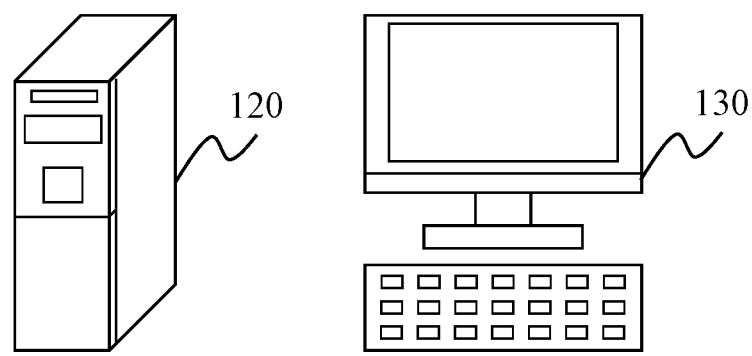
Figure 1:
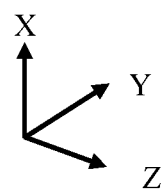

FIG. 1 is a schematic diagram illustrating an exemplary imaging system according to some embodiments of the present disclosure. In some embodiments, the imaging system 100 may scan an object and obtain corresponding scanning data. The imaging system 100 may generate an image based on the scanning data. The imaging system 100 may preprocess the scanning data or the generated image. The preprocessing of the scanning data or the generated image may include noise reduction, smoothing, correction, or the like, or any combination thereof.

In some embodiments, the imaging system 100 may be a medical imaging system. The medical imaging system may be a single modal imaging system or a multi modal imaging system. The single modal imaging system may include a PET (Positron Emission Tomography) device, a SPECT (Single Photon Emission Computed Tomography) device, a CT (Computed Tomography) device, an MRI (Magnetic Resonance Imaging) device, a digital radiography) device, etc. The multimodal imaging system may include a PET-CT device, a PET-MRI device, a SPECT-MRI device, etc.

As shown in FIG. 1, the imaging system 100 may include a scanning device 110, a controlling device 120 and a display device 130. The scanning device 110 may include a gantry 112, a table 114, a radioactive scanning source 116 and a detector 118. The gantry 112 may support the detector 118 and the radioactive scanning source 116. The table 114 may hold an object (e.g., patient). In some embodiments, the table 114 may move along the Z axis. The movement speed of the table 114 may be adjusted based on scanning time, scanning area, etc.

The radioactive scanning source 116 may emit radioactive rays to the object. The radioactive rays may include microparticle rays, photon rays, etc. The microparticle rays may include neutrons, protons, electrons, μ medium, heavy ions, or the like, or any combination thereof. The photon rays may include X-rays, γ-rays, α-rays, β-rays, ultraviolet, lasers, or the like, or any combination thereof.

The detector 118 may receive radioactive rays that transmit through the object and generate readings (also referred to as scanning data) corresponding to the received radioactive rays. In some embodiments, the detector 118 may include a scintillation detector (e.g., a cesium iodide detector), a gas detector, a circular detector, a square detector, an arcuate detector, or the like, or any combination thereof. In some embodiments, the detector may be a single-row detector or a multi-row detector. In some embodiments, the detector 118 may be connected to one or more sensors. The one or more sensors may detect one or more parameters (e.g., temperature, humidity, etc.) of the detector 118.

The controlling device 120 may process data and/or information obtained from the scanning device 110 and/or the display device 130. For example, the controlling device 120 may process the data from the detector 118. In some embodiments, the controlling device 120 may be a single server or a server group. The server group may be centralized or distributed. In some embodiments, the controlling device 120 may be local or remote. For example, the controlling device 120 may access information and/or data stored in the scanning device 110, and/or the display device 130 via a network. As another example, the controlling device 120 may be directly connected to the scanning device 110 and/or the display device 130 to access stored information and/or data. In some embodiments, the controlling device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the controlling device 120 may be implemented by a computing device 200 having one or more components as illustrated in FIG. 2.

In some embodiments, the controlling device 120 may obtain a first relationship between a focal point position of an X-ray tube and a thermal capacity of the X-ray tube. The controlling device 120 may also obtain a second relationship between a focal point position (or an offset of a focal point position) of the X-ray tube and a grid voltage difference of a focusing cup of the X-ray tube. In some embodiments, the controlling device 120 may obtain a working thermal capacity and compare the working thermal capacity with a reference thermal capacity to assess a difference of the two. Based on the difference in the thermal capacity and the first relationship, the controlling device 120 may obtain an offset of the focal point position. In some embodiments, the controlling device 120 may determine a grid voltage difference or a change of grid voltage difference that is needed to correct the offset based on the offset of the focal point position and the second relationship. The corrected focal point position may coincide with the reference focal point position.

The display device 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the display device 130 may be part of the controlling device 120.

In some embodiments, the display device 130 may include a user interface. The user interface may include one or more input or output devices, such as a touch screen, a keyboard, a microphone, a touch pad, etc. For example, a user may preset a first thermal capacity of the X-ray tube (also referred to as a reference thermal capacity) via the user interface of the display device 130. In some embodiments, the first thermal capacity may range between 0 and 20 percent of a maximum thermal capacity of the X-ray tube. For example, the first thermal capacity of the X-ray tube may be 15 percent of a maximum thermal capacity of the X-ray tube, or 0.75 MHU, or other values. In some embodiments, the display device 130 may generate an instruction for adjusting the X-ray tube based on a user input. The instruction for adjusting the X-ray tube may be generated based on an offset of a focal point position. In some embodiments, the user input may include a text, a voice, a press of a button, a touch or operation on the display device 130, etc.

In some embodiments, when a user intends to adjust the focal point position of the X-ray tube of a scanning device, the user may provide an input by pressing a button, inputting texts or voices via the display device 130. Then the imaging system 100 (e.g., the controlling device 120) may generate an instruction based on the input. The focal point position may be adjusted based on the instruction.

FIG. 2 is a schematic diagram illustrating an exemplary hardware and software components of a computing device according to some embodiments of the present disclosure.

The computing device 200 may be a general purpose computer or a special purpose computer, both may be used to implement an imaging system of the present disclosure. In some embodiments, the controlling device 120 may be implemented on the computing device 200, via its hardware, software program, firmware, or a combination thereof. For example, the computing device 200 may obtain a first relationship between a focal point position of an X-ray tube of a scanning device and a thermal capacity of the X-ray tube. The computing device 200 may also obtain a second relationship between a focal point position (or an offset of focal point position) of the X-ray tube and a grid voltage difference of the focusing cup of the X-ray tube. As another example, the computing device 200 may obtain a working thermal capacity and compare the working thermal capacity with a reference thermal capacity to assess a difference of the two. Based on the difference in the thermal capacity and the first relationship, the computing device 200 may obtain an offset of the focal point position. Although only one such computer is shown, for convenience, the computer functions relating to the CT imaging as described herein may be implemented in a distributed manner on a number of similar platforms, to distribute the processing load.

The computing device 200, for example, may include COM ports 250 connected to and from a network connected thereto to facilitate data communications. The computing device 200 may also include a central processing unit (CPU) 220, in the form of one or more processors, for executing program instructions. The exemplary computer platform may include an internal communication bus 210, program storage and data storage of different forms, for example, a disk 270, and a read only memory (ROM) 230, or a random access memory (RAM) 240, for various data files to be processed and/or transmitted by the computer. The exemplary computer platform may also include program instructions stored in the ROM 230, RAM 240, and/or other type of non-transitory storage medium to be executed by the CPU 220. The methods and/or processes of the present disclosure may be implemented as the program instructions. The computing device 200 also includes an I/O component 260, supporting input/output between the computer and other components therein such as user interface elements 280. The computing device 200 may also receive programming and data via network communications.

The computing device 200 may also include a hard disk controller communicated with a hard disk, a keypad/keyboard controller communicated with a keypad/keyboard, a serial interface controller communicated with a serial peripheral equipment, a parallel interface controller communicated with a parallel peripheral equipment, a display controller communicated with a display, or the like, or any combination thereof.

Merely for illustration, only one CPU and/or processor is described in the computing device 200. However, it should be note that the computing device 200 in the present disclosure may also include multiple CPUs and/or processors, thus operations and/or method steps that are performed by one CPU and/or processor as described in the present disclosure may also be jointly or separately performed by the multiple CPUs and/or processors. For example, if in the present disclosure the CPU and/or processor of the computing device 200 executes both operation A and operation B, it should be understood that operation A and operation B may also be performed by two different CPUs and/or processors jointly or separately in the computing device 200 (e.g., the first processor executes operation A and the second processor executes operation B, or the first and second processors jointly execute operations A and B).

Figure 3:
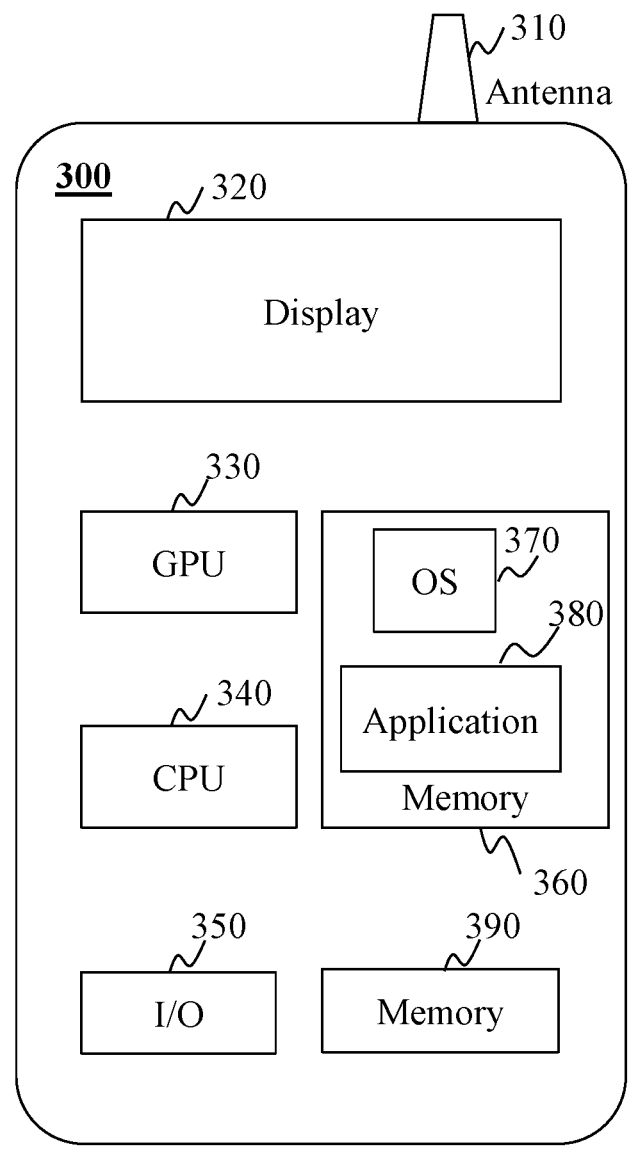
FIG. 3 is a schematic diagram illustrating an exemplary hardware and/or software components of an exemplary mobile device that is configured to implement a specific system disclosed in the present disclosure.

FIG. 3 is a schematic diagram illustrating an exemplary hardware and/or software components of an exemplary mobile device that is configured to implement a specific system disclosed in the present disclosure. As illustrated in FIG. 3, the mobile device 300 may include an antenna 310, a display 320, a graphic processing unit (GPU) 330, a CPU 340, an I/O 350, a storage 360, and a memory 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 390 from the storage 360 in order to be executed by the CPU 340. The applications 380 may include a browser or any other suitable mobile apps for receiving and rendering information relating to image processing or other information from the controlling device 120. User interactions with the information stream may be achieved via the I/O 350 and provided to the controlling device 120 and/or other components of the imaging system 100 via the network.

For example, the mobile device 300 may be used to preset a first thermal capacity of the X-ray tube (also referred to as a reference thermal capacity). In some embodiments, the first thermal capacity may range between 0 and 20 percent of a maximum thermal capacity of the X-ray tube. For example, the first thermal capacity may be 15 percent of a maximum thermal capacity of the X-ray tube, or 0.75 MHU, or other values. As another example, the mobile device 300 may receive or generate an instruction for adjusting the X-ray tube. The instruction for adjusting the X-ray tube may be generated based on an offset of a focal point position. The offset of the focal point position may be associated with the thermal capacities, grid voltage differences, etc. The instruction may be generated in response to a user input. The user input may include a text, a voice, a touch or operation on a screen, a press of a button, etc.

In some embodiments, when a user intends to adjust a focal point position of the X-tube of a scanning device, the user may provide an instruction for adjusting the focal point position by pressing a button, inputting texts or voices via the mobile device 300. Then the imaging system 100 (e.g., the controlling device 120) may adjust the focal point position based on the instruction.

In order to implement various modules, units and their functions described above, a computer hardware platform may be used as hardware platforms of one or more elements (e.g., the controlling device 120 and/or other sections of the system 100 described in FIG. 1). Since these hardware elements, operating systems and program languages are common; it may be assumed that persons skilled in the art may be familiar with these techniques and they may be able to provide information required in the imaging according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computer device. Thus, extra explanations are not described for the Figures.

Figure 4:
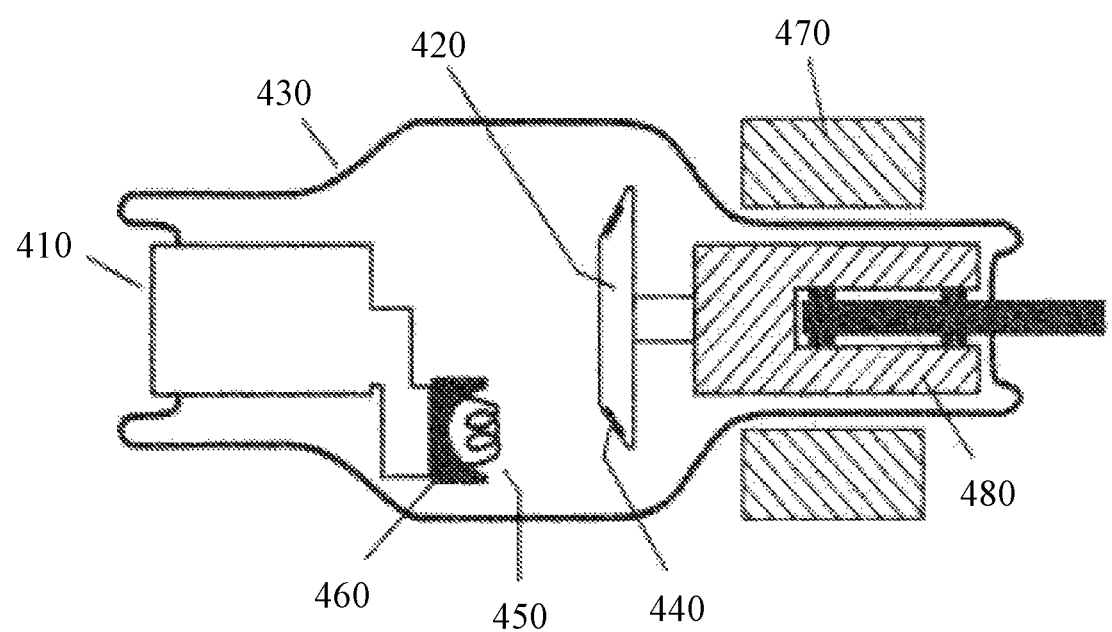
FIG. 4 is a schematic diagram illustrating an exemplary X-ray tube according to some embodiments of the present disclosure.

FIG. 4 is a schematic diagram illustrating an exemplary X-ray tube according to some embodiments of the present disclosure.

As shown in FIG. 4, the X-ray tube may include a cathode 410, an anode 420, and an envelope 430. The cathode 410 may be configured to emit and focus electrons. In some embodiments, the cathode 410 may include a filament 450, a focusing cup 460, and a voltage generator (not shown in the figure). In some embodiments, the cathode 410 may include a large filament and a small filament. The large filament that provides a large focal point may be used for scanning a tissue with a large volume or a large surface area, or for a scanning of a low resolution. The small filament that provides a small focal point may be used for scanning a tissue of a small volume or a thin layer (also referred to as a thin-layer scanning), or for a scanning of a high resolution.

Because the electrons are negatively charged, the electrons may repel each other and become scattered when they move toward the anode 420. In some embodiments, the focusing cup 460 may focus the scattered electrons into an electron beam. The electron beam may strike at the anode 420 with a specific size and/or shape. The shape may include a point, a circle, a ring, a rectangle, etc.

In some embodiments, the focusing cup 460 may include two grid voltages, and the difference of the two grid voltages (also referred to as a grid voltage difference) may affect the focal point position. In some embodiments, a relationship between the grid voltage difference and the focal point position (also referred to as a second relationship) may be determined. In some embodiments, a grid voltage difference may be obtained based on a focal point position and the second relationship. For example, if a focal point position shifts as disclosed elsewhere in the present disclosure, by adjusting the grid voltage difference based on the second relationship and the offset of the focal point position, the shifted focal point position may be corrected.

The voltage generator may generate a voltage difference across the filament 450. When the voltage difference or a temperature of the filament 450 reaches a specific level, a filament voltage may reach an effective value, and the filament 450 may emit the electrons. In some embodiments, the effective value of the filament voltage may vary between 5V and 10V.

The anode 420 may receive the electrons. In some embodiments, the anode 420 may be fixedly attached to the envelope 430. The anode 420 may include a target surface 440 that receives the electrons. The electrons may strike at the same position of the target surface 440 (also referred to as the focal point). In some embodiments, the anode 420 may be connected to a stator 470 and a rotor 480. As shown in FIG. 4, the stator 470 may be connected to the anode 420 and the envelope 430 such that the anode 420 may be fixed on the rotor 480. The rotor 480 may allow the anode 420 to rotate perpendicular to the incoming direction of the electrons. The electrons may strike at different positions of the target surface 440 when the target surface 440 of the X-ray tube rotates. For instance, the focal point where the electrons strike may have a shape of a ring. In some embodiments, the anode 420 may generate X-rays in response to the electrons.

In some embodiments, the cathode 410 may be spaced apart from the target surface 440 of the anode 420. The anode 420 may have a positive voltage relative to the cathode 410. The electrons emitted from the cathode 410 may be accelerated when they travel towards the target surface 440 due to the voltage difference between the anode 420 and the cathode 410. Descriptions regarding the measurement of the focal point position on the target surface 440 may be found elsewhere in the present disclosure. See, e.g., FIG. 5 and the description thereof.

In some embodiments, the focal point position may shift which in turn may cause artifacts in a reconstructed image. The shift or offset of the focal point position may be caused by mechanical reasons. For example, when the thermal capacity of the anode of the X-ray tube increases, the bearings or other mechanical structures of the X-ray tube may change, e.g., an angle or position of the target surface 440 may change. Such a change may cause a shift or offset of the focal point position. More descriptions of the offset of the focal point position may be found elsewhere in the present disclosure. See, e.g., FIG. 5 and the description thereof.

In some embodiments, the target surface 440 may be square or rectangular. A thickness of the target surface 440 may vary between 1.5 mm and 3 mm. The envelope 430 may be a hollow structure that houses the cathode 410 and the anode 420. The envelope 430 may be made of glass, ceramic, cermet, etc. In some embodiments, the envelope 430 may be sealed and a vacuum environment may be maintained in the X-ray tube 130. In some embodiments, the filament 450 may be heated and the vacuum environment may facilitate the movement of the electrons to the anode 420.

In some embodiments, the generated X-rays may be transmitted through a tube collimator (also referred to as a pre-patient collimator). In some embodiments, a filter may be arranged before the pre-patient collimator to absorb low-energy X-rays (also referred to as soft rays). The low-energy X-rays may increase the radiation dose an object undergoing or the scanning is subject to but usually do not generate effective scanning data. By such filtering, the overall radiation dose of X-rays on the object may be reduced and the quality of the scanning data and the reconstructed image may be unaffected or increased. The filter may include a flat filter, a bow-tie filter, etc. The filter may be adjusted based on different types of objects, e.g., children, adults, etc.

The tube collimator may be configured to shape and collimate the X-rays to a desired width. The detector 118 may detect X-rays that transmit through the object and reach the detector 118. In some embodiments, the readings (or scanning data) on the detector 118 may be proportional to the intensity of the detected X-rays. An image of the object may be reconstructed based on the readings on the detector 118. In some embodiments, a detector collimator (also referred to as a post-patient collimator) may be placed in front of the detector 118. The tube collimator and the detector collimator may have corresponding pin holes of similar sizes such that the X-rays passing through both may have a narrow and constant beam width.

In some embodiments, a focal point position may be measured via a pin hole in the tube collimator. The X-rays illuminated from the focal point may cover an area of the detector. The controlling device 120 may obtain a span of the area, a perpendicular distance between the pin hole in the collimator and the detector, and a perpendicular distance between the target surface and the detector. The controlling device 120 may obtain the focal point position based on the span and the two distances by employing the pin hole imaging theory (also referred to as the focal shift theory).

Figure 5:
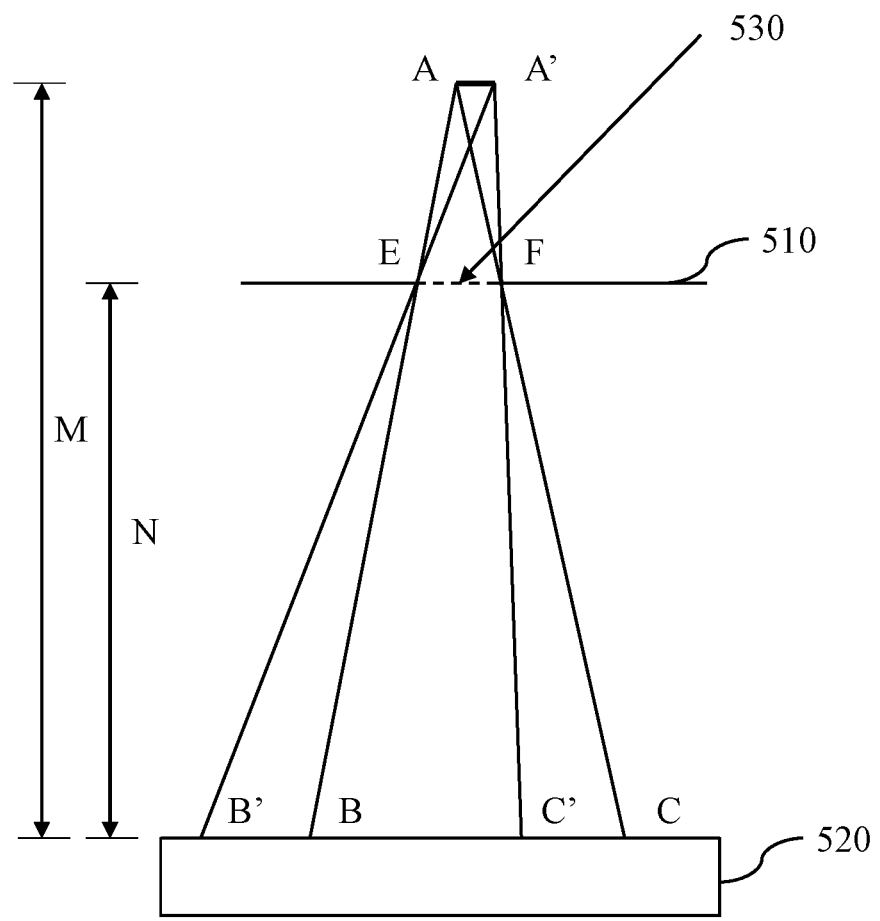
FIG. 5 is a schematic diagram illustrating an offset of a focal point position according to some embodiments of the present disclosure.

FIG. 5 is a schematic diagram illustrating an offset of the focal point position according to some embodiments of the present disclosure.

As shown in FIG. 5, a collimator 510 may include a hole 530. The hole 530 may have a specific size and shape. The size and shape of the hole 530 may correspond to the size and the shape of the focal point. In some embodiments, X-rays may be transmitted from an X-ray tube (not shown in the figure) to a detector 520 through the collimator 510. In some embodiments, an object may be placed between the collimator 510 and the detector 520. In some embodiments, the detector 520 may correspond to the detector 118 in connection with FIG. 1. The object may be a patient, or a portion thereof. For instance, the object may be a tissue or an organ of a patient, e.g., brain, chest, lung, leg, etc. The collimator 510 may be a tube collimator (also referred to as a pre-patient collimator). In some embodiments, a detector collimator (or a post-patient collimator) may be placed between the detector 520 and the tube collimator. In some embodiments, the intensity of the X-rays may be absorbed by the object and reduced. The intensity of the X-rays detected by the detector 520 in different regions of the object may be different due to different absorption rates of X-rays of the different regions. Information of the inside of the object (e.g., patient) may be acquired based on the distribution of the X-ray intensities. The distribution may be presented in the form of, e.g., an image.

In some embodiments, A may be a reference position of a focal point (e.g. a theoretic position of the focal point with respect to reference settings or original settings of the X-ray tube.) In some embodiments, the thermal capacity of the X-ray tube corresponding to the reference position A may be set manually or automatically, or measured by the system 100. A' may be an offset position of the focal point (also referred to as a working position that is affected by the thermal capacity of the X-ray tube). For example, when the thermal capacity of the X-ray tube reaches a specific level, the bearings or other structural components of the X-ray tube may change and cause the focal point to shift from A to A'. If the image is reconstructed with the offset focal point, the reconstructed image may be inaccurate or contain artifacts.

In some embodiments, the focal point position may be acquired based on the pinhole imaging theory (or referred to as the focal shift theory). For example, segment BC may represent a span of a theoretic area that the X-rays cover on the detector 520. Segment B'C' may represent a span of an area that the X-rays cover on the detector 520 when the focal point position shifts to A'. M may represent a perpendicular distance between the focal point position and the detector 520. N may represent a perpendicular distance between the hole 530 on the collimator 510 and the detector 520. In some embodiments, segment BC, segment B'C', M, and N may be measured by the imaging system 100, and then segment AA' (also referred to as an offset distance of the focal point position) may be obtained. In some embodiments, the offset distance may relate to the thermal capacity of the X-ray tube and may be corrected by adjusting the grid voltage difference of the focusing cup 460. More descriptions regarding the correction of the offset distance may be found elsewhere in the present disclosure. See, e.g., FIG. 10, and the description thereof.

Figure 6:
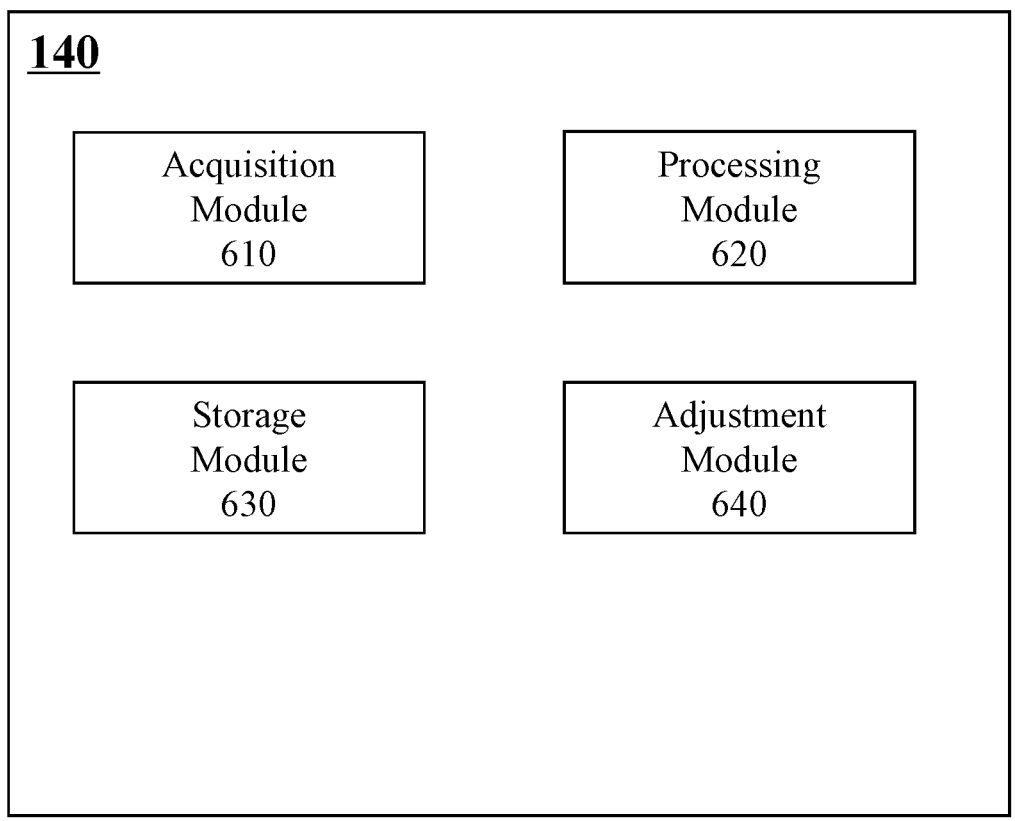
FIG. 6 is a schematic block diagram illustrating an exemplary controlling device according to some embodiments of the present disclosure.

FIG. 6 is a schematic block diagram illustrating an exemplary controlling device according to some embodiments of the present disclosure.

The controlling device 120 may include an acquisition module 610, a processing module 620, a storage module 630, and an adjustment module 640.

The acquisition module 610 may be configured to acquire information related to the X-ray tube. The information may include data of thermal capacities of the X-ray tube. The thermal capacities of the X-ray tube may be heat storage capacities of the X-ray tube. In some embodiments, the information may also include a maximum thermal capacity of the X-ray tube. The maximum thermal capacity of the X-ray tube may be a maximum heat storage capacity of the X-ray tube. For example, the anode 420 may be damaged if the thermal capacity of the X-ray tube excesses the maximum thermal capacity. In some embodiments, the thermal capacity of the X-ray tube may include a first thermal capacity ($Hs\_0$), a second thermal capacity ($Hs'$), and a plurality of third thermal capacities ($Hs\_1$, $Hs\_2$, $Hs\_3$, . . . $Hs\_n$). In some embodiments, the first thermal capacity of the X-ray tube may be set manually by a user or automatically by the system 100. Alternatively or additionally, the first thermal capacity of the X-ray tube may be determined based on a relationship between the thermal capacity and the focal point position of the X-ray tube (also referred to as a first relationship). A thermal capacity, e.g., the first thermal capacity, the second thermal capacity, a third thermal capacity, may be expressed in the form of a normalized or dimensionless value. For instance, a thermal capacity may be expressed as a ratio between the actual value of a thermal capacity and the actual value of the maximum thermal capacity. For example, the first thermal capacity of the X-ray tube may be a reference thermal capacity, e.g., 5 percent of the maximum thermal capacity, 15 percent of the maximum thermal capacity, 20 percent of the maximum thermal capacity, etc. The second thermal capacity of the X-ray tube may be a working thermal capacity, e.g., a value between 15 percent of the maximum thermal capacity and 90 percent of the maximum thermal capacity, when the imaging system 100 is performing a scan. Alternatively or additionally, the first thermal capacity, the second thermal capacity, and the third thermal capacities may be dimensional values, e.g., 0.75 MHU, 1 MHU, 2 MHU, etc. The third thermal capacities (also referred to as training thermal capacities) may be used for training purposes. The third thermal capacities may be used for determining the first relationship.

The processing module 620 may be configured to process information. The processing module 620 may determine the first relationship between a focal point position and a thermal capacity of the X-ray tube. To this end, a plurality of focal point positions and corresponding thermal capacities of the X-ray tube may be obtained. The focal point positions and the corresponding thermal capacities of the X-ray tube may be measured directly. In some embodiments, the first relationship may exist in form of a table, a curve, a database, etc. More descriptions of the determination of the first relationship may be found elsewhere in the present disclosure. See, e.g., FIGS. 8 and 11 and the description thereof.

The processing module 620 may determine a focal point position corresponding to a thermal capacity based on the first relationship. For instance, a first position (also referred to as a first focal point position or a reference focal point position) that corresponds to the first thermal capacity of the X-ray tube may be directly measured by the imaging system 100, e.g., by a process disclosed in FIG. 5. Alternatively or additionally, the first position may be determined based on the first relationship and the first thermal capacity. In some embodiments, a second position (also referred to as a second focal point position) may be determined based on the first relationship and a second thermal capacity. In some embodiments, the second focal point position or a difference between the first position and the second position (also referred to as an offset value or an offset of the focal point position) may first be determined based on the first thermal capacity of the X-ray tube, the second thermal capacity of the X-ray tube and the first relationship.

The storage module 630 may be configured to store the information. The information may include the first relationship, the first position and the second position of the X-ray tube, etc. The storage module 630 may also store the second relationship. The first relationship and the second relationship may be obtained by the acquisition module 610 from a device or module outside the imaging system 100 or may be obtained from a device or module inside the imaging system 100 (e.g., the processing module 620). The first relationship may refer to a relationship between a thermal capacity and a focal point position of an X-ray tube of a scanning device. The second relationship may refer to a relationship between a focal point position and a grid voltage difference of a focusing cup 460 of an X-ray tube of a scanning device. In some embodiments, the storage may further store a third relationship. For example, the third relationship may be a relationship between a thermal capacity and a grid voltage difference of the focusing cup 460 of the X-ray tube.

The adjustment module 640 may adjust the X-ray tube based on the extracted relationship, a working condition of the system 100 including, for example, a working thermal capacity of the X-ray tube, a working focal point position (or referred to as a second focal point position) of the X-ray tube, instructions provided by the system 100 or a user, or the like, or a combination thereof.

Figure 7:
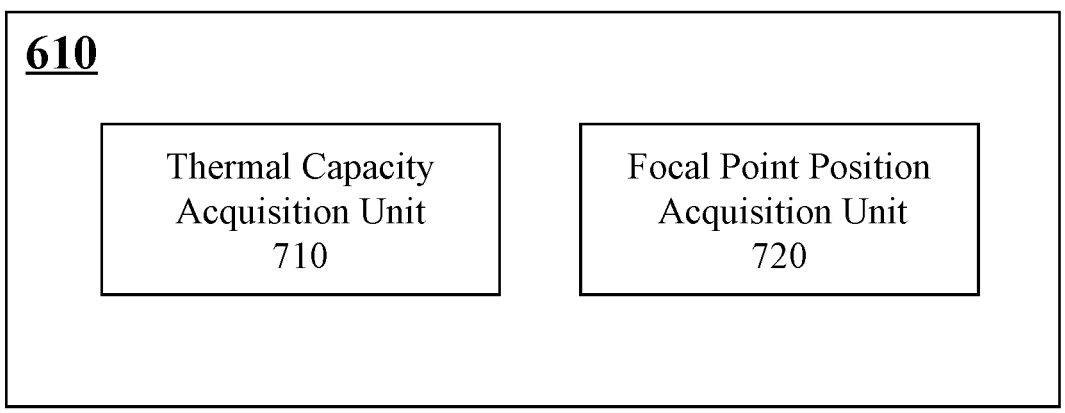
FIG. 7 is a schematic block diagram illustrating an exemplary acquisition module according to some embodiments of the present disclosure.

FIG. 7 is a schematic block diagram illustrating an acquisition module according to some embodiments of the present disclosure.

The acquisition module 610 may include a thermal capacity acquisition unit 710 and a focal point position acquisition unit 720.

The thermal capacity acquisition unit 710 may be configured to obtain thermal capacities of the X-ray tube including, for example, a second thermal capacity Hs', a plurality of third thermal capacities $Hs\_1, Hs\_2, Hs\_3, \ldots Hs\_n$, etc. A third thermal capacity $Hs\_1, Hs\_2, Hs\_3, \ldots Hs\_n$ may be in the form of a normalized or dimensionless value, e.g., a ratio between the actual value of a thermal capacity and the maximum thermal capacity of the X-ray tube. For example, a third thermal capacity may be 15 percent of the maximum thermal capacity, 20 percent of the thermal capacity, 25 percent of the maximum thermal capacity, 30 percent of the maximum thermal capacity, 35 percent of the maximum thermal capacity, etc. Alternatively or additionally, a third thermal capacity may be a dimensional value, e.g., 0.8 MHU, 1 MHU, 1.2 MHU, etc. In some embodiments, the thermal capacity acquisition unit 710 may include a plurality of sensors to measure the values of the thermal capacity and a calculator to obtain a dimensionless thermal capacity normalized with respect to, for example, the maximum capacity.

The focal point position acquisition unit 720 may be configured to obtain focal point positions corresponding to thermal capacities. The focal point positions corresponding to the thermal capacities may be directly measured by the imaging system 100, e.g., by a process disclosed in FIG. 5. Alternatively or additionally, the focal point position may be determined based on the thermal capacities and the first relationship. More descriptions of the determination of the first relationship may be found elsewhere in the present disclosure. See, e.g., FIGS. 8 and 11 and the description thereof.

Figure 8:
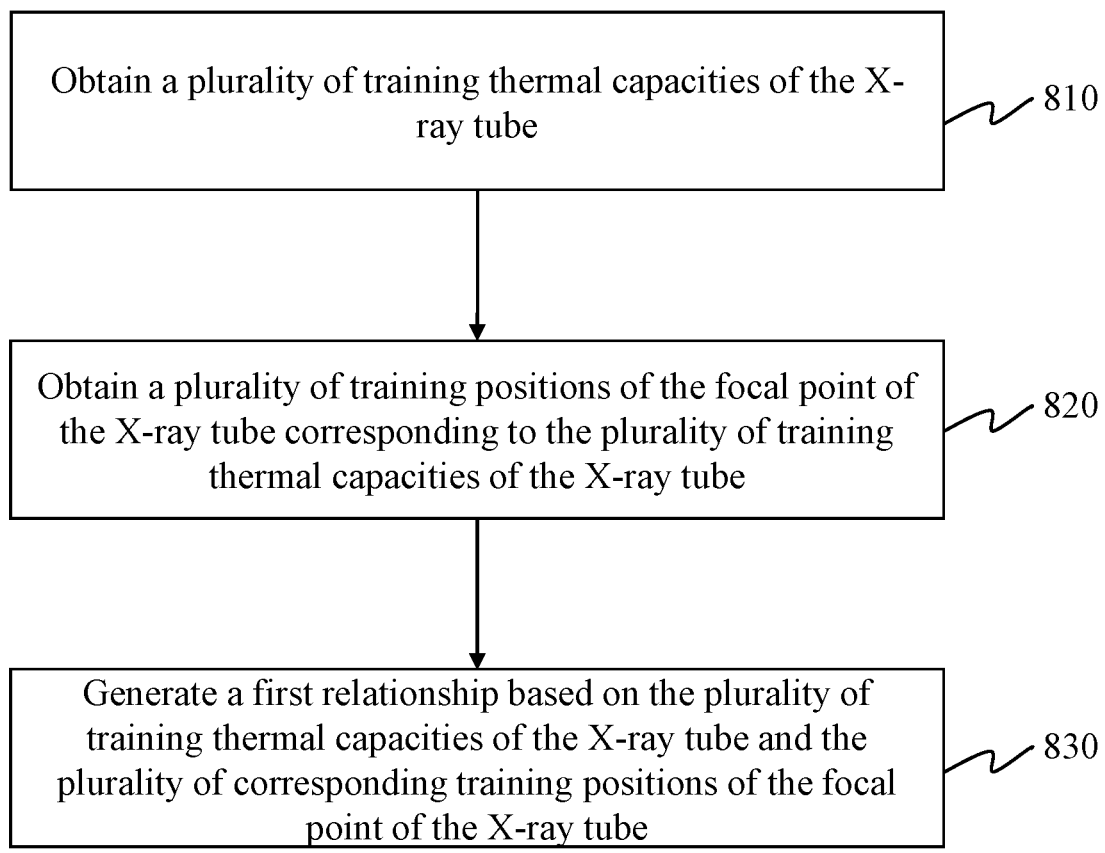
FIG. 8 is a flowchart of a process for determining a first relationship between a thermal capacity of an X-ray tube and a focal point position of the X-ray tube according to some embodiments of the present disclosure.

FIG. 8 is a flowchart of an exemplary process for determining a first relationship between a thermal capacity of an X-ray tube and a focal point position of the X-ray tube according to some embodiments of the present disclosure.

Operation 810 may include obtaining a plurality of training thermal capacities of the X-ray tube (e.g., the third thermal capacities). In some embodiments, 810 may be performed by the acquisition module 610. In some embodiments, 810 may also include obtaining the maximum thermal capacity of the X-ray tube and determining ratios between the plurality of training thermal capacities and the maximum thermal capacity of the X-ray tube. The plurality of training thermal capacities of the X-ray tube may be set manually by a user or automatically by the system 100. For example, the plurality of training thermal capacities may be dimensionless values, e.g., 15 percent of the maximum thermal capacity, 20 percent of the maximum thermal capacity, 25 percent of the maximum thermal capacity, 30 percent of the maximum thermal capacity, etc. As another example, the plurality of thermal capacities of the X-ray tube may be dimensional values, e.g., 0.8 MHU, 1 MHU, 1.2 MHU, etc.

Operation 820 may include obtaining a plurality of training focal point positions of the X-ray tube corresponding to the plurality of training thermal capacities of the X-ray tube. The plurality of training focal point positions corresponding to the plurality of training thermal capacities may be directly measured by the imaging system 100, e.g., by a process disclosed in FIG. 5. For example, the imaging system 100 may obtain a current thermal capacity and a corresponding focal point position.

Operation 830 may include generating the first relationship based on the plurality of training thermal capacities of the X-ray tube and the plurality of corresponding training focal point positions of the X-ray tube. Operation 830 may be implemented by the processing module 620. The first relationship may be presented in the form of a table, a curve, a database, a trained model, etc. A focal point position corresponding to a thermal capacity may be determined based on the first relationship. The first relationship may be determined by, for example, mapping, curve fitting, interpolating, machine learning, etc.

Merely by way of example, the first relationship may be determined by the interpolating. A plurality of training thermal capacities (or referred to as third thermal capacities) of the X-ray tube and corresponding training focal point positions of the X-ray tube may be obtained. For a training thermal capacity and its corresponding focal point position, an offset value of the training focal point position from a reference focal point position may be determined. The reference focal point position (or referred to as a first focal point position) may correspond to the reference thermal capacity (also referred to as a first thermal capacity). Based on the training focal point positions or the offset values between the training focal point positions and the reference position of the focal point, the first relationship between a focal point position or an offset value between the focal point and the reference focal point position and a thermal capacity of the X-ray tube may be determined. More descriptions of the first relationship by interpolation may be found elsewhere in the present disclosure. See, e.g., FIG. 11 and the description thereof.

As another example, a model may be trained by the training thermal capacities and their corresponding training focal point positions. A working position of the focal point may be obtained by applying a corresponding thermal capacity to the determined first relationship in the form of, for example, a curve, a table, a trained model, etc.

Figure 9:
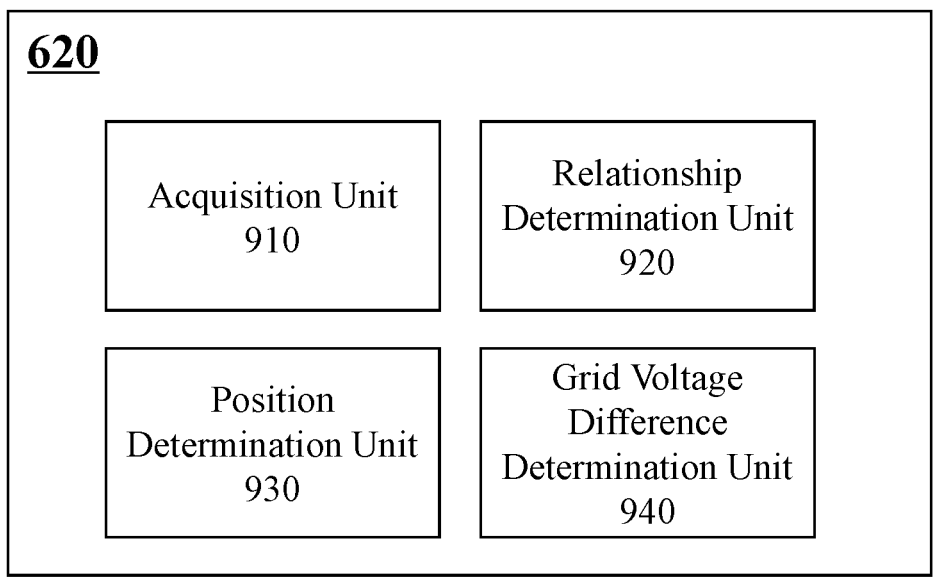
FIG. 9 is a schematic block diagram illustrating an exemplary processing module according to some embodiments of the present disclosure.

FIG. 9 is a schematic block diagram illustrating an exemplary processing module according to some embodiments of the present disclosure.

The processing module 620 may include an acquisition unit 910, a relationship generation unit 920, a position determination unit 930, and a grid voltage difference determination unit 940. The acquisition unit 910 may be configured to acquire information. The information may include thermal capacity of the X-ray tube. In some embodiments, the thermal capacity of the X-ray tube may be measured by a plurality of sensors, such as temperature sensors, humidity sensors, etc. The plurality of sensors may generate a plurality of readings and the acquisition unit 910 may generate a thermal capacity of the X-ray tube based on the readings of the sensors. The thermal capacities of the X-ray tube may include a first thermal capacity (or referred to as a reference thermal capacity) (Hs_0), a second thermal capacity (or referred to as a working thermal capacity of the X-ray tube when it is working or operating) (Hs'), a plurality of third thermal capacities (Hs_1, Hs_2, Hs_3 Hs_n) of the X-ray tube, etc.

The relationship determination unit 920 may determine a first relationship of the X-ray tube. Methods of determining the first relationship may include mapping, curve fitting, interpolating, machine learning, etc. For example, the first relationship may exist in form of table, curve, database, a training model, etc. One or more focal point positions corresponding to the one or more thermal capacities may be determined based on the first relationship. In some embodiments, a curve (or a table, a database) may be obtained based on third thermal capacities and focal point positions. Then a second position of focal point may be obtained based on a second thermal capacity and the curve (or the table, the database). As another example, a model may be trained by the third thermal capacities and focal point positions. Then a second position of focal point may be obtained based on a corresponding second thermal capacity and the model.

The position determination unit 930 may determine a working focal point position of the X-ray tube. The working focal point position of the X-ray tube may be directly measured by the imaging system 100, e.g., by a method disclosed in FIG. 5. Alternatively or additionally, the working focal point position may be determined based on the working thermal capacity and the first relationship. In some embodiments, the offset of the working focal point position from a reference focal point position may be determined. The working focal point position, or the offset of the working focal point position from the reference focal point position, may be applied to determine an adjustment that needs to be performed to compensate the offset. The compensation of the offset may be such that the adjusted working focal point position of the X-ray tube coincides with the reference focal point position. In some embodiments, the adjustment of the focal point position may be achieved by adjusting the grid voltage difference of the focusing cup 460 of the X-ray tube (e.g., the grid voltage difference of the focusing cup 460 of the X-ray tube).

The grid voltage difference determination unit 940 may determine a grid voltage difference based on the offset value of the focal point position (or the compensation of the offset value) and a second relationship. In some embodiments, the second relationship may be obtained based on a plurality of training grid voltage differences of a focusing cup 460 of an X-ray tube and the corresponding training focal point positions of the X-ray tube. For example, a plurality of training grid voltage differences may first be determined. For each of the plurality of training grid voltage differences, a corresponding training focal point position may be measured by, for example, the pin hole imaging theory disclosed elsewhere in the present disclosure. The second relationship may then be generated based on the plurality of training grid voltage differences and their corresponding training focal point positions. In some embodiments, the second relationship may be preset by a user via the display device 130, obtained by the acquisition module 610 from a device or module outside the imaging system 100, or obtained by the acquisition unit 910 from a device or module inside the imaging system 100.

The grid voltage difference may control the focal point position of the X-ray tube. The focal point position of the X-ray tube may be changed by adjusting the grid voltage difference of the focusing cup 460. In some embodiments, the adjustment module 640 may adjust one of the two grid voltages of the focusing cup 460, and hence adjust a difference between the two grid voltages (e.g., grid voltage difference).

Figure 10:
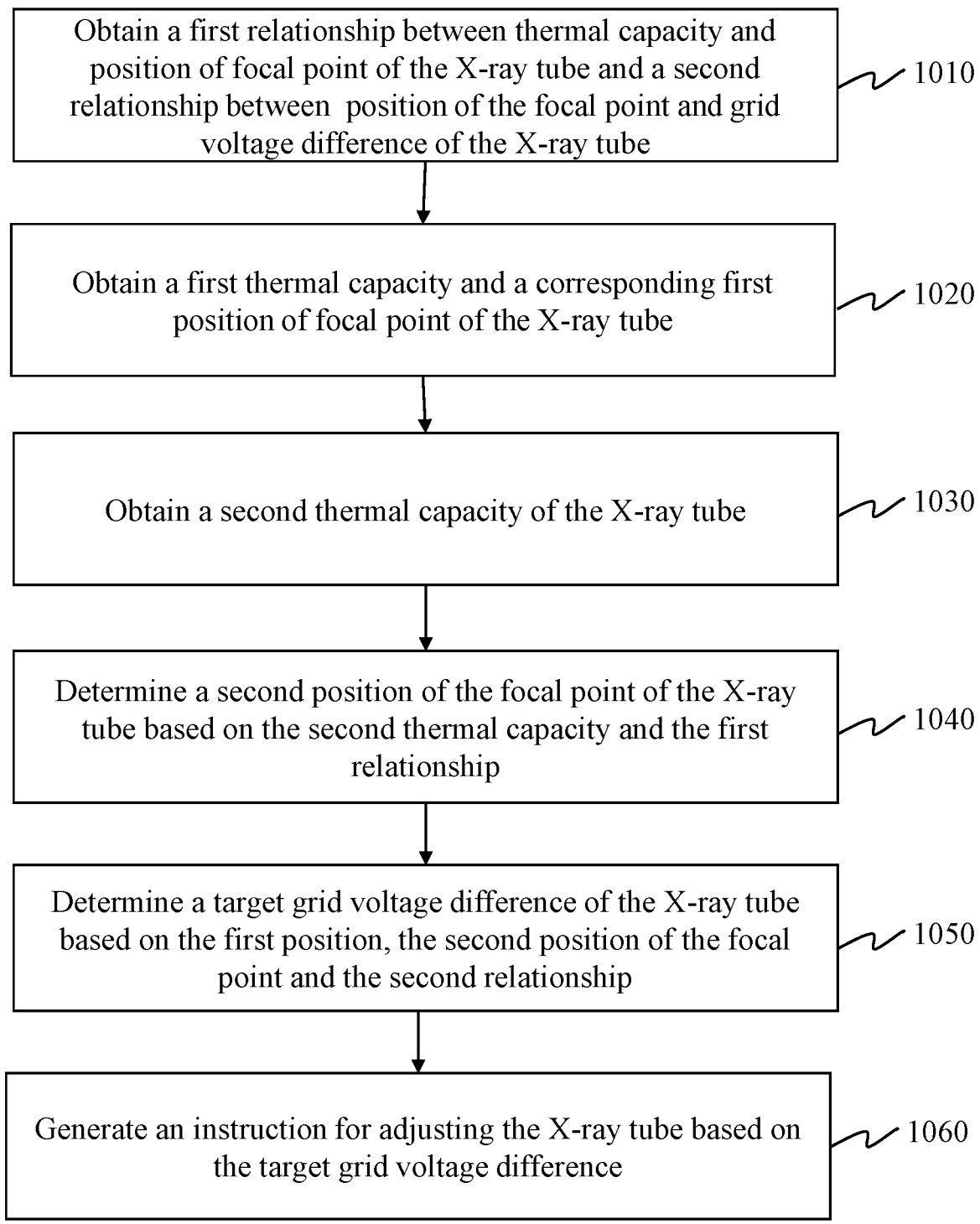
FIG. 10 is a flowchart of a process for adjusting grid voltage difference according to some embodiments of the present disclosure.

FIG. 10 is a flowchart of a process for adjusting a grid voltage difference according to some embodiments of the present disclosure.

Operation 1010 may include obtaining a first relationship and a second relationship. The first relationship and the second relationship may be obtained by the acquisition module 610 from a device or module outside the imaging system 100 or may be obtained from a device or module inside the imaging system 100 (e.g., the processing module 620). The first relationship may refer to a relationship between a thermal capacity and a focal point position of an X-ray tube of a scanning device. The second relationship may refer to a relationship between a focal point position and a grid voltage difference of a focusing cup 460 of an X-ray tube of a scanning device. In some embodiments, operation 1010 may further include obtaining a third relationship. For example, the third relationship may be a relationship between a thermal capacity and a grid voltage difference of the focusing cup 460 of the X-ray tube. Operation 1010 may be implemented by the relationship determination unit 920.

Operation 1020 may include obtaining a first thermal capacity (or referred to as a reference thermal capacity) and a corresponding first focal point position (or referred to as a reference focal point position) of an X-ray tube. Operation 1020 may be implemented by the acquisition unit 910. Merely by way of example, the first thermal capacity may be 15 percent of the maximum thermal capacity, 20 percent of the maximum thermal capacity of the X-ray tube, etc. The first position of the X-ray tube may correspond to the first thermal capacity of the X-ray tube. In some embodiments, the first thermal capacity of the X-ray tube may be set manually by a user of automatically by the system 100. Alternatively or additionally, the first thermal capacity of the X-ray tube may be determined based on the reference thermal capacity and the first relationship between a thermal capacity of the X-ray tube and a focal point position of the X-ray tube.

Operation 1030 may include obtaining a second thermal capacity (or a working thermal capacity) of the X-ray tube. Operation 1030 may be implemented by the acquisition unit 910. Merely by way of example, the second thermal capacity may range from 15 percent of the maximum thermal capacity to 90 percent of the maximum thermal capacity. Alternatively or additionally, the second thermal capacity may be a dimensional value, e.g., 0.75 MHU, 1 MHU, 2 MHU, etc.

Operation 1040 may include determining a second position of the X-ray tube based on the second thermal capacity and the first relationship. Operation 1040 may be implemented by the position determination unit 930. More descriptions of the second position of the X-ray tube may be found elsewhere in the present disclosure. See, e.g., FIG. 11 and the description thereof.

Operation 1050 may include determining a target grid voltage difference based on the first position, the second position, and the second relationship. Operation 1050 may be implemented by the grid voltage difference determination unit 940. More descriptions of the grid voltage difference may be found elsewhere in the present disclosure. See, e.g., FIG. 12 and the description thereof.

Merely by way of example, the target grid voltage difference may correspond to an offset of a working focal point position from a reference focal point position. One of two gird voltages of the focusing cup 460 may be adjusted based on the target grid voltage and compensate the offset. The compensation of the offset may be such that the adjusted working focal point position of the X-ray tube coincides with the reference focal point position.

Operation 1060 may include generating an instruction for adjusting the X-ray tube based on the target grid voltage difference. In some embodiments, the focal point position of the X-ray tube may be adjusted from the second position to the first position by adjusting the grid voltage of the focusing cup 460 based on the target grid voltage difference. In some embodiments, the X-ray tube of the scanning device 110 may be adjusted based on the instruction.

It should be noted that the above description of adjusting grid voltage difference is provided for the purposes of illustration, and not intended to limit the scope of the present disclosure. For persons having ordinary skills in the art, the process may be modified or altered in forms and details under the teaching of the present disclosure. However, those modifications and alterations are within the scope of the above description. For example, operations 1020 and 1030 may be performed before operation 1010. In some embodiments, any other selection condition may be added between any two operations, e.g., storage and backup process for the result of any operation.

Figure 11:
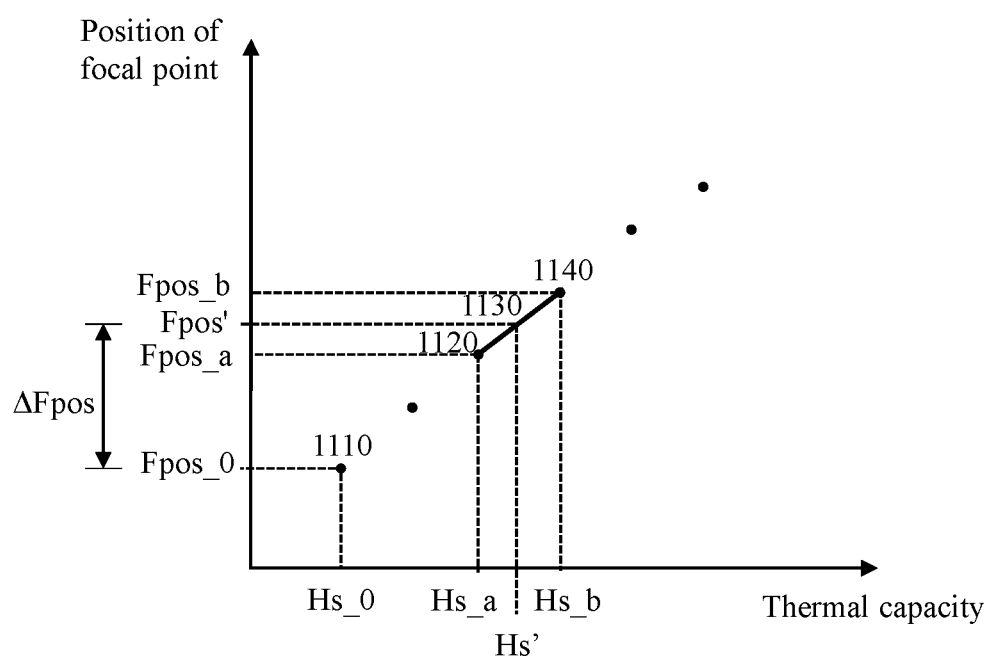
FIG. 11 is a schematic diagram illustrating an exemplary first relationship between a thermal capacity of an X-ray tube and a focal point position of an X-ray tube according to some embodiments of the present disclosure.

FIG. 11 is a schematic diagram illustrating the first relationship between a thermal capacity of an X-ray tube and a focal point position of the X-ray tube according to some embodiments of the present disclosure.

As shown in FIG. 11, the horizontal axis may represent a thermal capacity of an X-ray tube, and the vertical axis may represent a focal point position of the X-ray tube. Merely by way of example, point 1110 may correspond to a first thermal capacity Hs_0, and point 1130 may correspond to a second thermal capacity Hs'. The first thermal capacity may be a reference thermal capacity. The second thermal capacity may be a working thermal capacity measured by the system 100. In some embodiments, the focal point position of point 1130 Fpos' may be unknown or difficult to be directly measured.

In some embodiments, other points, as shown in FIG. 11, including points 1120 and 1140 (whose vertical coordinates are Fpos_a and Fpos_b, respectively), may correspond to training thermal capacities. The training thermal capacities may be training thermal capacities used for determining the first relationship between a thermal capacity and a focal point position of the X-ray tube.

In some embodiments, the focal point position of point 1130 Fpos' may be obtained based on its thermal capacity Hs' and the first relationship. For example, the Fpos' may be obtained by an linear interpolating method with following formula:

$$Fpos'=Fpos\_a-(Hs\_a-Hs')\times(Fpos\_a-Fpos\_b)\div(Hs\_a-Hs\_b), \quad (1)$$

wherein Hs_a and Hs_b may be two of the training thermal capacities that are close to the Hs' and Fpos_a and Fpos_b may be the training focal point positions corresponding to Hs_a and Hs_b respectively.

In some embodiment, if there exists a training thermal capacity that is the same as or sufficiently close to Hs', Fpos' may be determined as the focal point position corresponding to that third thermal capacity.

In some embodiments, a curve representing a relationship between a thermal capacity and a focal point position may be obtained by curve fitting based on a plurality of third thermal capacities and their corresponding focal point positions. The curve fitting may include constructing a curve that has an acceptable fit to the points according to one or more mathematical functions including, for example, exponential functions, logarithmic functions, trigonometric functions, power functions, etc. The Fpos' may be obtained based on the curve and Hs'.

In some embodiments, a model may be trained based on a plurality of third thermal capacities (or referred to as training thermal capacities) and their corresponding third focal point positions (or referred to as training focal point positions) by one or more machine learning techniques. Exemplary machine learning techniques may include supervised learning, unsupervised learning, semi-supervised learning, a regression algorithm, instance-based learning, a regularization algorithm, a Bayes algorithm, a kernel based learning algorithm, a clustering algorithm, rule-based learning, neural network, deep learning, an order-reducing algorithm, a hybrid algorithm, etc. By inputting Hs' to the trained model, Fpos' may be generated.

Figure 12:
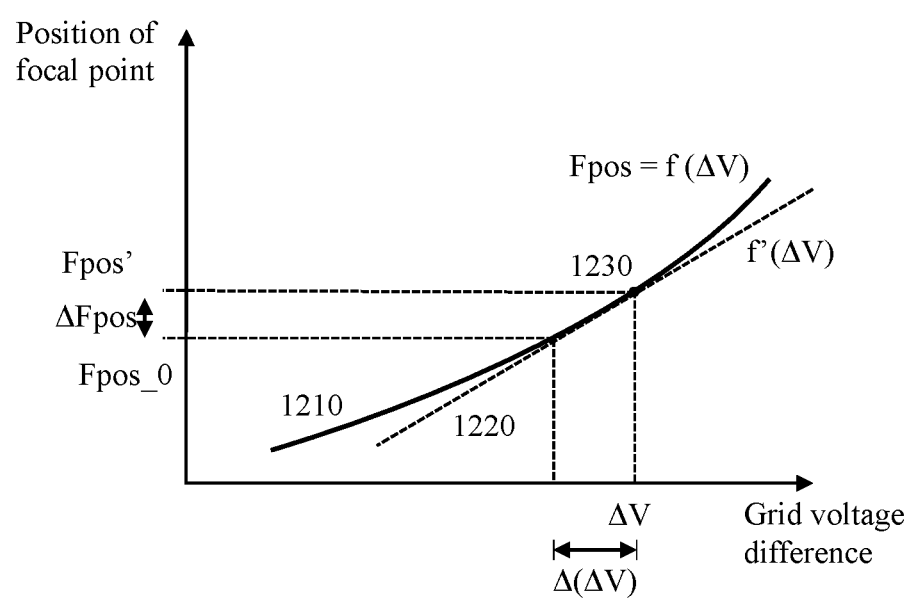
FIG. 12 is a schematic diagram illustrating an exemplary second relationship between a focal point position of an X-ray tube and a grid voltage difference according to some embodiments of the present disclosure.

FIG. 12 is a schematic diagram illustrating an exemplary second relationship between a focal point position of an X-ray tube and a grid voltage difference of the focusing cup of the X-ray tube according to some embodiments of the present disclosure.

As shown in FIG. 12, the horizontal axis may represent a grid voltage difference of the focusing cup 460 of the X-ray tube, and the vertical axis may represent a focal point position. As shown in FIG. 12, function 1210 $f(\Delta V)$ may represent a relationship between the grid voltage difference and the focal point position (also referred to as the second relationship) of the X-ray tube. In some embodiments, the function 1210 may be a straight line, e.g., a first order function. Alternatively, the function 1210 may be a curve, e.g., a second or higher order function, a proportional function, a reversely proportional function, a trigonometric function, an exponential function, a logarithm function, etc. In some embodiments, the function 1210 may be obtained from an external source outside the imaging system 100. Alternatively or additionally, the function 1210 may be obtained from a storage component inside the imaging system 100 (e.g., storage module 630). In some embodiments, the second relationship may be obtained based on a plurality of reference grid voltage differences and their corresponding focal point positions or offsets of the focal point positions from a reference focal point position by mapping, interpolation, curve fitting, machine learning, etc. In some embodiments, the second relationship describes the relation between an offset of a focal point position from a reference focal point position (or a compensation of such an offset) and a grid voltage difference.

As shown in FIG. 12, point 1230 may correspond to a focal point position Fpos', which may represent a working focal point position with an offset. Fpos_0 may represent a reference focal point position. ΔFpos may be a difference there between or the offset of Fpos' from Fpos_0. In some embodiments, a value of an adjustment of grid voltage difference $\Delta(\Delta V)$ (or grid voltage difference that is needed to compensate or correct the offset ΔFpos) may be obtained based on the function 1210, the working focal point position Fpos', and/or ΔFpos.

In some embodiments, a function 1220 $f'(\Delta V)$ which is a first-order derivate of $f(\Delta V)$ may be obtained. The function 1220 may also represent a gradient of the function 1210. In some embodiments, the value of an adjustment of grid voltage difference $\Delta(\Delta V)$ to compensate ΔFpos may be obtained by following formula:

$$\Delta(\Delta V) = \Delta Fpos \div f'(\Delta V). \quad (2)$$

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a specific feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the specific features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A method implemented on at least one device including at least one processor and at least one computer-readable storage medium, the method comprising:
   obtaining a first thermal capacity of an anode of an X-ray tube and a first position of a focal point of the X-ray tube;
   obtaining a second thermal capacity of the anode of the X-ray tube, wherein the second thermal capacity is different from the first thermal capacity;
   obtaining a first relationship between a position of the focal point and a thermal capacity of the anode of the X-ray tube;
   determining a second position of the focal point of the X-ray tube based on the second thermal capacity and the first relationship;
   determining a target grid voltage difference of a focusing cup of the X-ray tube based on the first position and the second position of the focal point, wherein the target grid voltage difference is a difference between a first grid voltage of a first section of the focusing cup and a second grid voltage of a second section of the focusing cup; and
   adjusting the grid voltage difference of the focusing cup based on the target grid voltage difference.

2. The method of claim 1, wherein the first thermal capacity is a reference thermal capacity and the second thermal capacity is a working thermal capacity.

3. The method of claim 1, wherein the first thermal capacity ranges between 0 and 20 percent of a maximum thermal capacity of the anode of the X-ray tube.

4. The method of claim 1, wherein the obtaining a first relationship between a position of the focal point and a thermal capacity of the anode of the X-ray tube comprises:
   obtaining a plurality of training thermal capacities of the anode of the X-ray tube;
   obtaining a plurality of training positions of the focal point of the X-ray tube, wherein each of the plurality of training positions of the focal point of the X-ray tube corresponds to one of the plurality of training thermal capacities of the anode of the X-ray tube, respectively; and
   identifying the first relationship based on the plurality of training thermal capacities of the anode of the X-ray tube and the plurality of corresponding training positions of the focal point of the X-ray tube.

5. The method of claim 4, wherein the obtaining a plurality of training positions of the focal point comprises:
   measuring a training position of the focal point via a pin hole in a collimator of the X-ray tube.

6. The method of claim 4, wherein the identifying the first relationship comprises:
   performing mapping, curve fitting, interpolating, or machine learning based on the plurality of training thermal capacities of the anode of the X-ray tube and the plurality of corresponding training positions of the focal point of the X-ray tube.

7. The method of claim 4, wherein the obtaining a first position of the focal point of an X-ray tube comprises:
   determining the first position of the focal point based on the thermal capacity and the first relationship.

8. The method of claim 1, wherein the determining a second position of the focal point comprises:
   obtaining two training thermal capacities of the anode of the x-ray tube, wherein a first training thermal capacity of the two training capacities is greater than the second thermal capacity and a second training thermal capacity of the two training capacities is less than the second thermal capacity;
   obtaining two training positions of the focal point of the X-ray tube corresponding to the two training thermal capacities of the anode of the X-ray tube; and
   determining, using a linear interpolation method, the second position of the X-ray tube based on the second thermal capacity of the anode of the X-ray tube, the two training thermal capacities of the anode of the X-ray tube, and the two corresponding training positions of the focal point of the X-ray tube.

9. The method of claim 1, wherein the determining a target grid voltage difference of a focusing cup of the X-ray tube comprises:
   obtaining a second relationship between a grid voltage difference of the focusing cup of the X-ray tube and a position of the focal point of the X-ray tube; and
   determining the target grid voltage difference of the focusing cup of the X-ray tube based on the first position and the second position of the focal point of the X-ray tube and the second relationship.

10. The method of claim 1, wherein the adjusting the grid voltage difference of the focusing cup comprises adjusting the focal point of the X-ray tube from the second position to the first position.

11. A system, comprising:
   at least one computer-readable storage medium including a set of instructions; and
   at least one processor in communication with the at least one computer-readable medium, wherein when executing the set of instructions, the system is caused to:

obtain a first thermal capacity and a second thermal capacity of an anode of an X-ray tube, wherein the second thermal capacity is different from the first thermal capacity;
obtain a first position of a focal point of the X-ray tube;
obtain a first relationship between a position of the focal point and a thermal capacity of the anode of the X-ray tube;
determine a second position of the focal point of the X-ray tube based on the second thermal capacity and the first relationship;
determine a target grid voltage difference of a focusing cup of the X-ray tube based on the first position and the second position of the focal point, wherein the target grid voltage difference is a difference between a first grid voltage of a first section of the focusing cup and a second grid voltage of a second section of the focusing cup; and
adjust the grid voltage difference of the focusing cup based on the target grid voltage difference.

12. The system of claim 11, wherein the first thermal capacity is a reference thermal capacity and the second thermal capacity is a working thermal capacity.

13. The system of claim 11, wherein to obtain the first relationship between a position of the focal point and a thermal capacity of the anode of the X-ray tube, the system is caused to:
obtain a plurality of training thermal capacities of the anode of the X-ray tube;
obtain a plurality of training positions of the focal point of the X-ray tube, wherein each of the plurality of training positions of the focal point of the X-ray tube corresponds to one of the plurality of training thermal capacities of the anode of the X-ray tube, respectively; and
identify the first relationship based on the plurality of training thermal capacities of the anode of the X-ray tube and the plurality of corresponding training positions of the focal point of the X-ray tube.

14. The system of claim 13, wherein to obtain a plurality of training positions of the focal point of the X-ray tube, the system is caused to:
measure a training position of the focal point via a pin hole in a collimator of the X-ray tube.

15. The system of claim 13, wherein to identify the first relationship, the system is caused to:

perform mapping, curve fitting, interpolating, or machine learning based on the plurality of training thermal capacities of the anode of the X-ray tube and the plurality of corresponding training positions of the focal point of the X-ray tube.

16. The system of claim 11, wherein to determine a target grid voltage difference of a focusing cup of the X-ray tube, the system is caused to:
obtain a second relationship between a grid voltage difference of the focusing cup of the X-ray tube and a position of the focal point; and
determine the target grid voltage difference of the focusing cup of the X-ray tube based on the first position and the second position of the focal point of an X-ray tube and the second relationship.

17. The system of claim 11, wherein to adjust the grid voltage difference of the focusing cup, the system is caused to:
adjust the focal point of the X-ray tube from the second position to the first position.

18. A non-transitory computer readable medium storing instructions, the instructions, when executed by a computer, causing the computer to implement a method, comprising:
obtaining a first thermal capacity of an anode of an X-ray tube and a first position of a focal point of the X-ray tube;
obtaining a second thermal capacity of the anode of the X-ray tube, wherein the second thermal capacity is different from the first thermal capacity;
obtaining a first relationship between a position of the focal point and a thermal capacity of the anode of the X-ray tube;
determining a second position of the focal point of the X-ray tube based on the second thermal capacity and the first relationship;
determining a target grid voltage difference of a focusing cup of the X-ray tube based on the first position and the second position of the focal point, wherein the target grid voltage difference is a difference between a first grid voltage of a first section of the focusing cup and a second grid voltage of a second section of the focusing cup; and
adjusting the grid voltage difference of the focusing cup based on the target grid voltage difference.

* * * * *